(12) United States Patent
Levine

(10) Patent No.: US 7,398,123 B1
(45) Date of Patent: Jul. 8, 2008

(54) METHODS AND DEVICES FOR REDUCING THE DETECTION OF INAPPROPRIATE PHYSIOLOGIC SIGNALS TO REDUCE MISDIAGNOSIS OF NORMAL RHYTHMS AS TACHYARRHYTHMIAS

(75) Inventor: Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 50 days.

(21) Appl. No.: 10/794,565

(22) Filed: Mar. 5, 2004

(51) Int. Cl.
*A61N 1/368* (2006.01)

(52) U.S. Cl. ............................. 607/14; 607/9

(58) Field of Classification Search ........... 607/4, 607/9, 14, 15
See application file for complete search history.

(56) References Cited

U.S. PATENT DOCUMENTS

| | | | |
|---|---|---|---|
| 4,515,161 A | 5/1985 | Wittkampf et al. | |
| 5,584,867 A | 12/1996 | Limousin et al. | |
| 5,591,214 A | 1/1997 | Lu | |
| 5,658,320 A | 8/1997 | Betzold et al. | 607/14 |
| 5,735,881 A | 4/1998 | Routh et al. | 607/14 |
| 6,122,545 A | 9/2000 | Struble et al. | |
| 6,438,421 B1* | 8/2002 | Stahmann et al. | 607/9 |
| 6,477,416 B1* | 11/2002 | Florio et al. | 607/9 |
| 6,501,988 B2* | 12/2002 | Kramer et al. | 607/9 |
| 6,512,952 B2* | 1/2003 | Stahmann et al. | 607/9 |
| 6,611,714 B1 | 8/2003 | Mo | |
| 6,625,490 B1* | 9/2003 | McClure et al. | 607/9 |
| 6,643,547 B2 | 11/2003 | Kim | |
| 6,687,539 B2 | 2/2004 | Gilkerson et al. | 607/5 |
| 6,731,980 B1* | 5/2004 | Mouchawar et al. | 607/9 |
| 6,871,097 B1 | 3/2005 | Strandberg | 607/25 |
| 6,873,875 B1 | 3/2005 | Gilkerson et al. | |
| 6,934,585 B1 | 8/2005 | Schloss et al. | |
| 2002/0082650 A1* | 6/2002 | Stahmann et al. | 607/9 |
| 2002/0082653 A1 | 6/2002 | Stahmann et al. | 607/9 |
| 2002/0193835 A1 | 12/2002 | Baker | |
| 2004/0010295 A1* | 1/2004 | Kramer et al. | 607/25 |
| 2004/0049235 A1* | 3/2004 | Deno et al. | 607/9 |
| 2004/0210264 A1* | 10/2004 | Kleckner et al. | 607/25 |

(Continued)

FOREIGN PATENT DOCUMENTS

EP      1038548 A2     3/2000

(Continued)

OTHER PUBLICATIONS

Jürgen Schreieck et al., "Inappropriate Shock Delivery Due to Ventricular Double Detection with a Biventricular Pacing Implantable Cardioverter Defibrillator", PACE, vol. 24, No. 7; Jul. 2001, pp. 1154-1157.

(Continued)

*Primary Examiner*—George R. Evanisko
*Assistant Examiner*—Michael Kahelin

(57) ABSTRACT

Various embodiments can reduce mode switching in response to inappropriate but anticipated signals, such as far field R-waves. Additionally, various embodiments can also increase the alert period for detection of true atrial tachyarrhythmias in dual chamber pacing systems. Further, various embodiments can reduce mode switching or tachyarrhythmia response to same chamber delayed signals. In addition, various embodiments can increase the alert period for detection of true tachyarrhythmias in multisite pacing systems arising from the chamber being stimulated or sensed while minimizing repeated detection and counting of the same native depolarization or evoked response to effectively preclude mislabeling and detection of a normal rhythm as a tachycardia.

20 Claims, 13 Drawing Sheets

U.S. PATENT DOCUMENTS

2005/0125041 A1* 6/2005 Min et al. .................. 607/9

FOREIGN PATENT DOCUMENTS

| EP | 1038548 A3 | 3/2000 |
|---|---|---|
| WO | WO 97/11748 | 4/1997 |

OTHER PUBLICATIONS

Andre Queiroga, "Overdrive Pacing for Atrial Fibrillation—Complications and Ways to Overcome Them", Eurospace Supplements, vol. 2; Jun. 2001, pp. B203 (ABSTRACT).

David Kawanishi et al., "Closer Investigation of Oversensing: Sense Amplifier Signal Analysis", Eurospace Supplements, vol. 2; Jun. 2001, pp. B146 (ABSTRACT).

Final Office Action, mailed Apr. 16, 2007: Related U.S. Appl. No. 10/794,566, filed Mar. 5, 2004.

Restriction Requirement, mailed Jul. 11, 2005: Related U.S. Appl. No. 10/794,566.

NonOffice Action, mailed Aug. 25, 2005: Related U.S. Appl. No. 10/794,566.

NonFinal Office Action, mailed Dec. 2, 2005: Related U.S. Appl. No. 10/794,566.

NonFinal Office Action, mailed May 11, 2006: Related U.S. Appl. No. 10/794,566.

NonFinal Office Action, mailed Oct. 13, 2006: Related U.S. Appl. No. 10/794,566.

Final Office Action, mailed Mar. 26, 2007: Related U.S. Appl. No. 10/794,566.

Restriction Requirement, mailed Apr. 10, 2007: Related U.S. Appl. No. 10/792,082.

NonFinal Office Action, mailed Jul. 19, 2007: Related U.S. Appl. No. 10/792,082.

* cited by examiner

Depolarization  1  2

Ventricular capture of Chamber 1

Sensing of the Chamber 1 paced complex
when conducted to Chamber 2

METHODS AND DEVICES FOR REDUCING THE DETECTION OF INAPPROPRIATE PHYSIOLOGIC SIGNALS TO REDUCE MISDIAGNOSIS OF NORMAL RHYTHMS AS TACHYARRHYTHMIAS

CROSS-REFERENCE TO RELATED APPLICATIONS

This application is related to copending U.S. patent application Ser. No. 10/794,566, titled "Methods and Devices for Reducing the Detection of Inappropriate Physiologic Signals to Reduce Misdiagnosis of Normal Rhythms as Tachyarrhythmias", filed concurrently herewith.

TECHNICAL FIELD

The present invention generally relates to implantable stimulation devices, such as pacemakers and implantable cardioverter defibrillators (ICDs).

BACKGROUND

Many contemporary implantable stimulation devices, such as pacemakers and ICDs, are typically designed to respond, in some manner, to tachyarrhythmias—which are essentially very fast heart rhythms. Stimulation devices are also designed with so-called refractory periods. A "refractory period" refers to an interval or timing cycle following a sensed or paced event during which the device's sense amplifier will not respond to incoming signals. Dual-chamber devices have separate refractory periods for each chamber (atrial and ventricular). The refractory period is designed into the stimulation devices to preclude the devices from responding to normal, but inappropriate signals (e.g. T-waves, evoked responses, etc.). The normal refractory periods, however, can preclude sensing of the very fast rates.

The refractory period can be segmented into two segments—the absolute refractory period and the relative refractory period. For a stimulation device, the absolute refractory period refers to the time period directly following a sensed or paced event during which all activity is ignored by the device's sense amplifier. The absolute refractory period is followed by the relative refractory period which refers to a "noise-sampling" or other detection portion during which sensing occurs, but the information is used for purposes other than resetting timing cycles. Examples of such purposes include atrial rate detection of Automatic Mode Switching and differentiation of a conducted atrial premature beat from a true PVC. Automatic Mode Switching or "AMS" refers to an algorithm which causes the pacemaker to revert from a tracking mode (e.g. DDD or VDD) to a non-tracking mode (e.g. DDI or VVI) upon recognition of a pathologic rapid intrinsic atrial rhythm. In order for the pacemaker (or pacemaker component of an ICD) to detect very rapid atrial rates that would normally be obscured or hidden by the normal PVARP (post-ventricular atrial refractory period) timing cycle, the current generation devices utilize a microprocessor to monitor events occurring within the PVARP. This allows recognition of very rapid atrial rhythms and engagement of AMS.

Accordingly, during the relative refractory period, the device can look to see if there are events that occur (e.g., fast atrial or ventricular rates) for which therapy or diagnosis is needed. There are certain events that can occur, however, that are otherwise normal, but which should not be counted for purposes of assessing whether there is a fast rate. For example, it is not uncommon to sense a ventricular depolarization (QRS complex) up in a lead positioned in the atrium. Yet if the device mistakenly counts this complex as an atrial event, the device may mistakenly determine that the patient is experiencing a rapid atrial rate. This can lead the device to provide erroneous diagnoses or administer inappropriate therapy.

Expanding on the previous example. A common physiologic but inappropriate signal that is detected is the far field R wave (FFRW). A FFRW is a ventricular depolarization that is also detected on the atrial channel. Commonly, the FFRW follows the sensed or paced ventricular event. Sensing the ventricular event initiates a timing circuit on the atrial channel designated the Post-Ventricular Atrial Blanking (PVAB) period. Recall that a blanking period is an interval during which the pacemaker is absolutely refractory—that is, it not capable of detecting any event. Hence, the standard method for managing FFRW signals is to program the PVAB to a sufficient duration to preclude detection of a FFRW if present.

Consider that one could arbitrarily program a very long PVAB, however, any period of blanking effectively blinds the pacemaker to appropriate events occurring during that interval and will, in the case of the AMS algorithm, either delay the recognition of an atrial tachyarrhythmia or totally prevent its recognition. Hence, one would prefer to keep the PVAB as short as possible.

A paper presented at Europace 2001, on 25 Jun. 2001, demonstrated a difference between the timing of FFRWs associated with either a native or paced ventricular complex. The paper was entitled *Closer investigation of oversensing: sense amplifier signal analysis*, Europace 2001; 2: Suppl B: B146 (abstract 454). In this paper, the interval between the sensed R wave and the FFRW detected on the atrial channel is termed the far field R wave duration (FFRD). In response to a sensed native R wave, the FFRD was 25 ms (bipolar) and 49 ms (unipolar). When one examined paced ventricular events, the FFRD with the paced R wave was 83 ms (bipolar) and 150 ms (unipolar).

A second paper also presented at Europace 2001, on 26 Jun. 2001, entitled *Overdrive pacing for atrial fibrillation—complications and ways to overcome them*, Europace 2001; 2: Suppl B: B203 (abstract 648), focused on a series of patients implanted with the Vitatron Selection® 900 pacemaker. It was noted that the FFRW between the detected native ventricular R wave and the detected atrial signal was relatively short, but since the PVAB had been programmed to an even shorter interval, inappropriate AMS occurred because the system interpreted the FFRW as a true P wave. When this was recognized by the clinicians, they increased the PVAB which, in turn, prevented AMS in response to FFRW associated with native R waves. The patient then developed some level of AV block such that the ventricular events were all paced. The patient again began experiencing AMS episodes shown to be inappropriate and due to FFRW sensing. The interval from the ventricular stimulus to the FFRW signal associated with ventricular pacing was 100 ms longer that the interval from the detected R wave to the FFRW signal. When the PVAB was increased further to preclude these inappropriate signals, inappropriate AMS episodes were prevented. However, now the system was utilizing a very long PVAB that compromised recognition of native atrial tachyarrhythmias.

In a second example, a biventricular ICD may detect depolarizations in both the right ventricle and the left ventricle in response to a single ventricular depolarization. This will result in double counting and the misidentification of a normal heart rhythm as a pathologic tachycardia resulting in the delivery of therapy that is inappropriate for the actual rhythm.

It would be desirable to protect against detecting inappropriate signals. The implantable stimulation device should certainly respond to appropriate rhythms, but the device should also avoid false triggering and/or false diagnostics.

Accordingly, this invention arose out of concerns associated with providing improved methods and systems for reducing detection of inappropriate physiologic signals.

SUMMARY

Various embodiments can reduce mode switching in response to inappropriate but anticipated signals, such as far field R-waves. Additionally, various embodiments can also increase the alert period for detection of true atrial tachyarrhythmias in dual chamber pacing systems. Further, various embodiments can reduce mode switching or tachyarrhythmia response to same chamber delayed signals. In addition, various embodiments can increase the alert period for detection of true tachyarrhythmias in multisite pacing systems.

DETAILED DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Exemplary Stimulation Device

The following description sets forth but one exemplary stimulation device that is capable of being used in connection with the various embodiments that are described below. It is to be appreciated and understood that other stimulation devices, including those that are not necessarily implantable, can be used and that the description below is given, in its specific context, to assist the reader in understanding, with more clarity, the inventive embodiments described herein.

Figure 1:
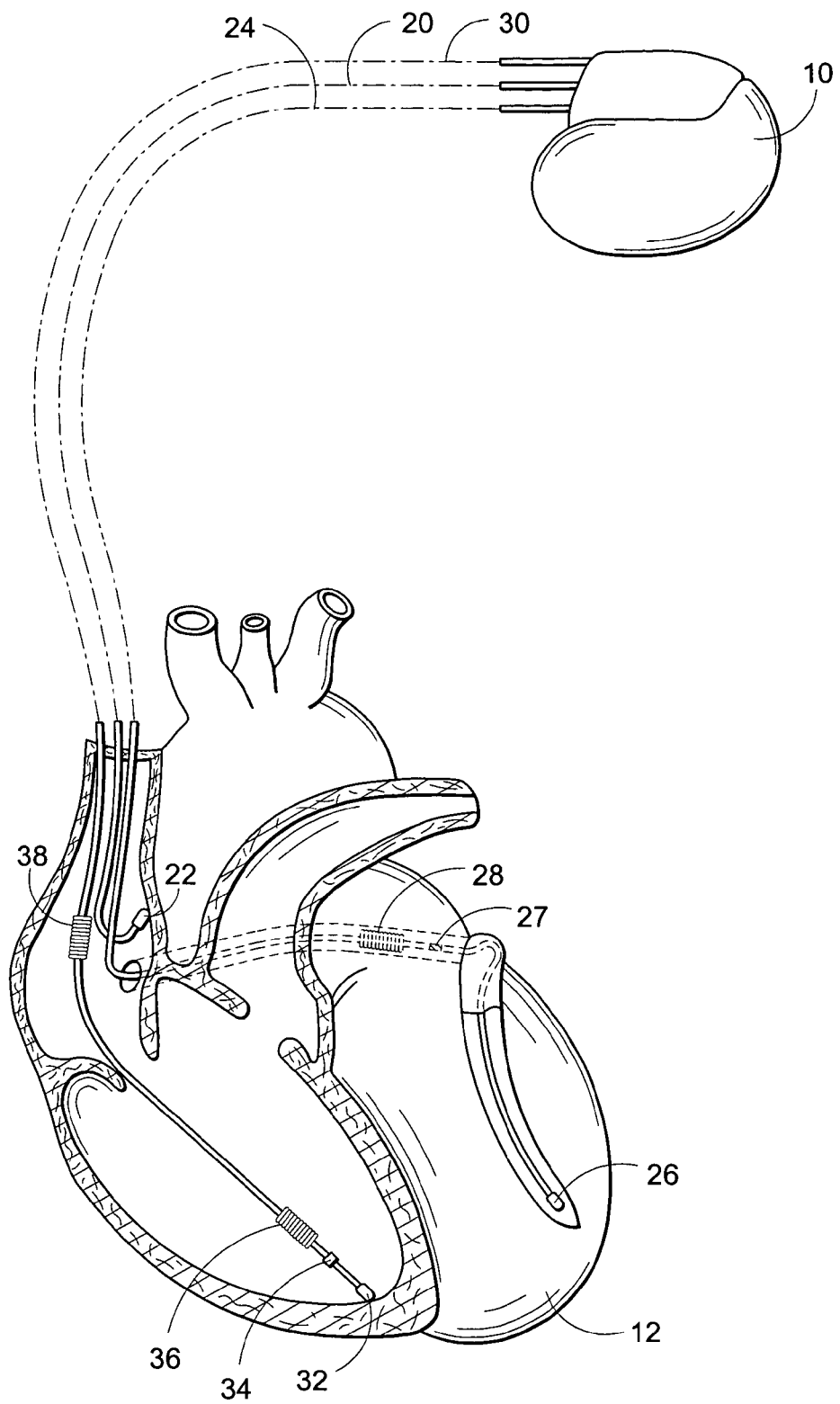
FIG. 1 is a simplified diagram illustrating an implantable stimulation device in electrical communication with at least three leads implanted into a patient's heart for delivering multi-chamber stimulation and shock therapy.

FIG. 1 shows an exemplary stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the venous vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

Stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
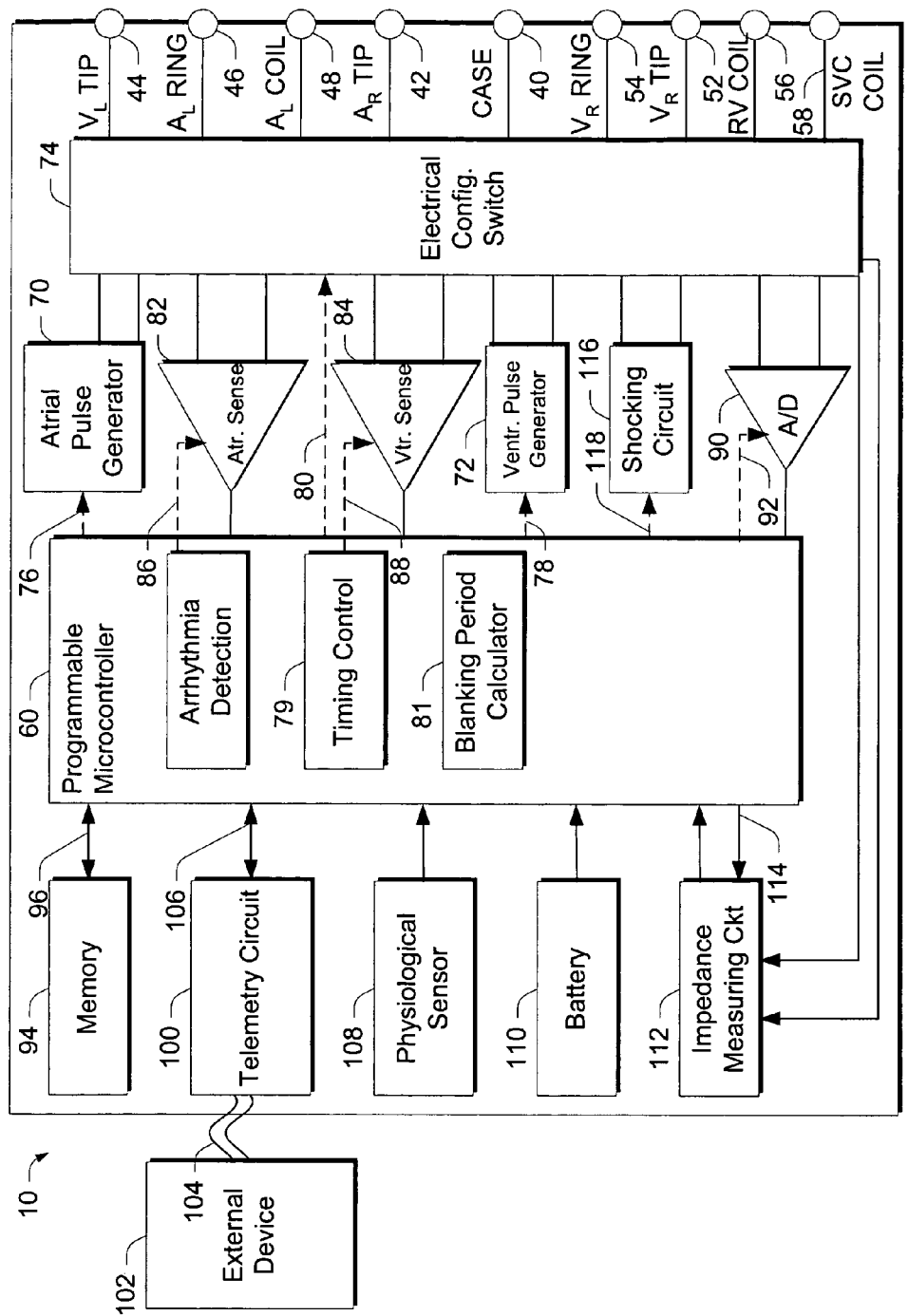
FIG. 2 is a functional block diagram of a multi-chamber implantable stimulation device illustrating exemplary basic elements of a stimulation device which can provide cardioversion, defibrillation and/or pacing stimulation in up to four chambers of the heart.

FIG. 2 shows an exemplary, simplified block diagram depicting various components of stimulation device 10. The stimulation device can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the inventive techniques and methods described below can be implemented in connection with any suitably configured or configurable stimulation device. Accordingly, one of skill in the art could readily duplicate, eliminate or disable the appropriate circuitry in any desired combination to provide a device capable of treating the appropriate chamber(s) with cardioversion, defibrillation and pacing stimulation.

Housing 40 for stimulation device 10 is often referred to as the "can", "case" or "case electrode", and may be programmably selected to act as the return electrode for all "unipolar" modes. Housing 40 may further be used as a return electrode alone or in combination with one or more of the coil electrodes 28, 36 and 38, for shocking purposes. Housing 40 further includes a connector (not shown) having a plurality of terminals 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal (VR TIP) 52, a right ventricular ring terminal (VR RING) 54, a right ventricular shocking terminal (RV COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design and operation of the microcontroller 60 are not critical to the described embodiments. Rather, any suitable microcontroller 60 may be used that carries out the functions described herein. The use of microprocessor-based control circuits for performing timing and data analysis functions are well known in the art.

FIG. 2 also shows an atrial pulse generator 70 and a ventricular pulse generator 72 which generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

Microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

A switch 74 includes a plurality of switches for connecting the desired electrodes to the appropriate I/O circuits, thereby providing complete electrode programmability. Accordingly, switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. Switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control (AGC), bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. Additionally, an improvement in AGC is automatic sensitivity control or ASC, which has been incorporated in current ICDs from the assignee of this document. ASC involves programming the device to a very sensitive setting but to preclude it from detecting known but inappropriate events occurring in close proximity to the end of the refractory period, it starts the sensitivity at a proportion of the total signal amplitude as detected and measured by the implanted device. This is termed Threshold Start. From this relatively insensitive setting, it progressively increases the sensitivity until it reaches the programmed sensitivity value. The progressive increase in sensitivity can also be delayed by a programmable duration. This is termed Decay Delay. This algorithm allows the implanted device to be very sensitive during the majority of the alert period but to be less sensitive early in the timing period when known but physiologically inappropriate events such as the terminal portion of the QRS or the T wave would be capable of being detected at the programmed sensitivity value.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similarly, "F-waves" or "Fib-waves" can also refer to supraventricular rhythms when they occur in the atrium. In the atrium, the predefined rate zone limits would be bradycardia, normal, atrial tachycardias (either low rate or high rate with high rate usually being atrial flutter) and atrial fibrillation rate zones. As in the ventricle, various other criteria can be applied such as sudden onset, stability, physiologic sensors and morphology, etc, in order to facilitate a diagnosis and determine the type of remedial therapy that might be warranted.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. This may be on the atrial or ventricular channel of the system. Alternatively, a capture threshold search can desirably be performed every 6 to 8 hours at least the acute phase (e.g., the first 30 days) and less frequently thereafter or perhaps, more frequently depending on the stability of the threshold or abrupt fluctuation in the capture threshold. A capture threshold search would begin at a desired starting point (either a high energy level or the level at which capture is currently occurring) and decrease the energy level until capture is lost. The output is then progressively increased in small steps, potentially of variable or programmable values. The value at which capture is regained is known as the capture threshold. Thereafter, a working margin is added to the capture threshold.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. One feature of the described embodiments is the ability to sense and store a relatively large amount of data (e.g., from the data acquisition system 90), which data may then be used for subsequent analysis to guide the programming of the device.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device 10 can further include a physiologic sensor 108, commonly referred to as a "rate-modulated" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc.

The stimulation device additionally includes a battery 110 that provides operating power to all of the circuits shown in FIG. 2. For the stimulation device 10, which employs shocking therapy, the battery 110 is capable of operating at low current drains for long periods of time (e.g. preferably less than 10 μA), and is capable of providing high-current pulses (for capacitor charging) when the patient requires a shock pulse (e.g. preferably, in excess of 2 A, at voltages above 2 V, for periods of 10 milliseconds or more). The battery 110 also desirably has a predictable discharge characteristic so that elective replacement time can be detected. Accordingly, the device 10 preferably employs a power source sufficient to deliver the high voltage shock therapy. One such example is the lithium/silver vanadium oxide battery, as is true for most (if not all) current devices capable of delivering high voltage therapy.

The stimulation device 10 can further include magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100. More recent systems do not require a magnet in the telemetry module to open a communication channel. In these newer systems, a magnet can be used to disable therapy (as in an ICD), trigger the device to store an electrogram (EGM) or other event counter data, assess battery status and others.

FIG. 2 also shows an impedance measuring circuit 112 which is enabled by the microcontroller 60 via a control signal 114. The known uses for an impedance measuring circuit 112 include, but are not limited to, lead impedance surveillance during the acute and chronic phases for mechanical integrity of the lead, measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

In the case where the stimulation device 10 is intended to operate as an implantable cardioverter/defibrillator (ICD) device, it detects the occurrence of an arrhythmia, and automatically applies an appropriate series of antitachycardia pacing pulses or an electrical shock therapy to the heart based on the device's diagnosis of the rhythm and the manner in which it was programmed to respond with the intent of terminating the detected arrhythmia. To this end, the microcontroller 60 further controls an atrial pacing circuit 70 by way of a control signal 76, the ventricular pacing circuit 72 by way of a control signal 78 and shocking circuit 116 by way of a control signal 118. The atrial pacing circuit 70 generates critically timed or bursts of pacing pulses delivered to the atrial electrodes 22, 22a, 27 and 27a to treat an atrial tachyarrhythmia. The ventricular pacing circuit 72 generates a critically time or burst of pacing pulses delivered to the ventricular electrodes 26, 32 and/or 34 to treat an organized ventricular tachyarrhythmia. In the setting of either fibrillation or very rapid organized tachycardias, the shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of an organized tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of ventricular fibrillation which is a very disorganized rapid ventricular arrhythmia. Accordingly, the microcontroller 60 is capable of controlling the synchronous or asynchronous delivery of the shocking pulses.

Overview

One of the objectives of some of the described embodiments is to maximize the alert period for recognition of true atrial or ventricular events (depending on the arrhythmia detection chamber), while minimizing the likelihood of "false triggers" from being misinterpreted as a pathologic tachyarrhythmia. With respect to Automatic Mode Switching, as the far field R wave duration (FFRD) differs between paced ventricular output and sensed R wave, the PVAB should be allowed to be programmable with respect to whether the initiating event is paced or sensed. This will eliminate the need to program the PVAB for the worse-case scenario which would be associated with ventricular pacing. When the ventricular event is a sensed event, the PVAB can be programmed to a shorter interval to maximize the detection period for atrial tachyarrhythmias. If the ventricular event is paced, the PVAB is automatically increased to the longer interval for that cycle.

This same concept of programmability of the absolute refractory period (blanking period) can be extended to multisite stimulation systems with respect to sensed events in the setting of parallel output systems, and with respect to sensed and paced events where both channels to the same relative chamber (atria or ventricles) are totally independent of one another.

Specifically, when utilizing multichamber or multisite atrial stimulation and sensing, (this is usually utilized in an effort to prevent pathologic atrial tachyarrhythmias), various embodiments described below provide a separate programmable atrial blanking period. This is in response to either an atrial paced event or an atrial sensed event, as there may be a significant delay between the first atrial event and detection of that event on the other atrial lead. If one does not provide this and there is delayed inter-atrial conduction, the detection of the second component of the same atrial event may be interpreted as a very rapid atrial rate to trigger a mode switch episode or delivery of atrial antitachycardia therapy comprised of either critically timed or bursts of pacing pulses or higher energy shocks. In systems which allow for multisite atrial pacing and sensing, various embodiments provide a programmable absolute atrial refractory period that differs between atrial sensed and atrial paced events. When there is independent pacing and sensing on each of two atrial leads, then a different absolute atrial refractory period can be provided based on whether the event on the first channel is paced or sensed. Where there is parallel rather than independent function associated with the two channels, then various embodiments allow for a programmable absolute atrial refractory period associated with a sensed atrial event. Special considerations are required when there is an atrial paced event in a parallel system, as the outputs will be delivered to both atrial leads at the same time and cause simultaneous depolarization at both atrial electrode sites unless the output to one chamber is subthreshold and does not capture. In this case, a very short detection window may allow for false identification of very rapid atrial rates based on the interval from the atrial stimulus to the P wave detected on the lead that failed to capture one of the atrial chambers.

When utilizing multichamber or multisite ventricular stimulation, various embodiments provide for different refractory periods on each ventricular channel depending on sensing or pacing on one channel with respect to the other channel. In biventricular ICDs, in the absence of triggered pacing where an event sensed on one leads results in a triggered output on the second lead, the system can misinterpret a normal rhythm as a tachycardia given the conduction delay between the two leads (the two cardiac chambers) resulting in double-counting. To prevent double counting of native signals, some biventricular ICDs in the past have designated sensing on only a single lead for arrhythmia identification to minimize the double counting phenomenon. This has potential limitations and can force competition of an ectopic event arising from the chamber which is disabled with respect to sensing. Although this complex will conduct to the other chamber (the sensed chamber), if an atrial stimulus occurs before this conduction is completed, there is a greater chance that the native R wave will coincide with the ventricular blanking period, not be sensed thus allowing for delivery of a ventricular output. Given the interventricular conduction delay, the stimulus delivered to the originating ventricular channel may coincide with the ventricular vulnerable period and induce a tachyarrhythmia. Hence, disabling sensing in one chamber, while this will minimize double counting, is a less than optimal solution.

As some background for appreciating the context of the inventive embodiments, consider FIGS. 3-10.

Figure 3:
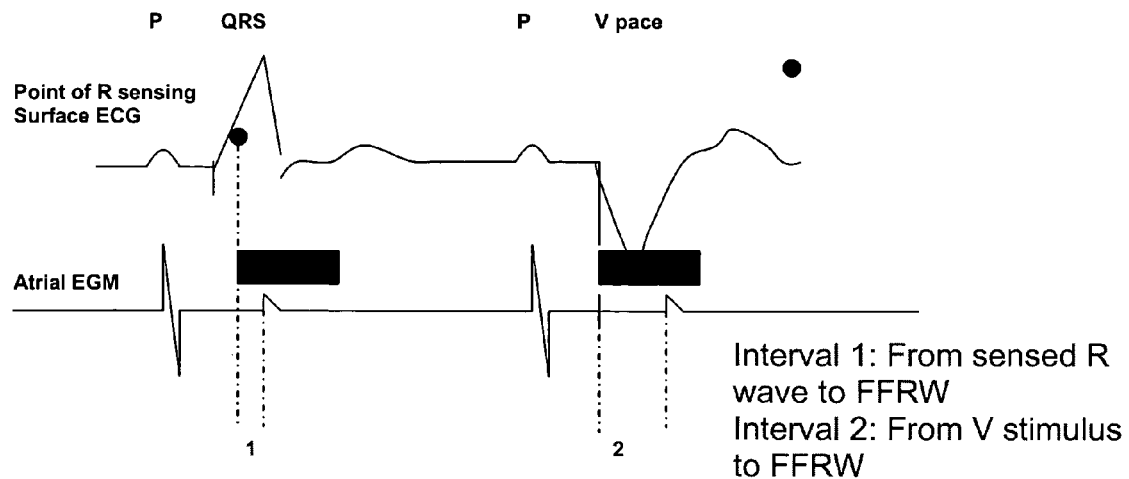
FIG. 3 is a schematic of a surface ECG, where the dot within the QRS complex is the point of sensing the complex.

FIG. 3 is a schematic of a surface ECG, where the dot within the QRS complex is the point of sensing the complex by the implanted device. The bottom line is the atrial EGM, where the large deflection is the large atrial signal associated with the atrial depolarization, and the very small triangular deflection is a schematic representation of the ventricular signal as seen on the atrial channel. Interval 1 represents the interval from the time from which the R wave is sensed by the pacemaker to the FFRW, and interval 2 represents the interval from a ventricular paced stimulus to the FFRW. The solid black box represents the length of the timing circuit called the post-ventricular atrial blanking period (PVAB). This is the absolute refractory period portion of the PVARP period. Notice that the PVAB is long enough to cover both the far field signal seen with a native QRS complex (i.e. interval 1), and the far field signal seen associated with a ventricular paced complex (i.e. interval 2). In the setting of ventricular sensing, however, the PVAB is too long and will compromise sensing some atrial tachyarrhythmias.

Figure 4:
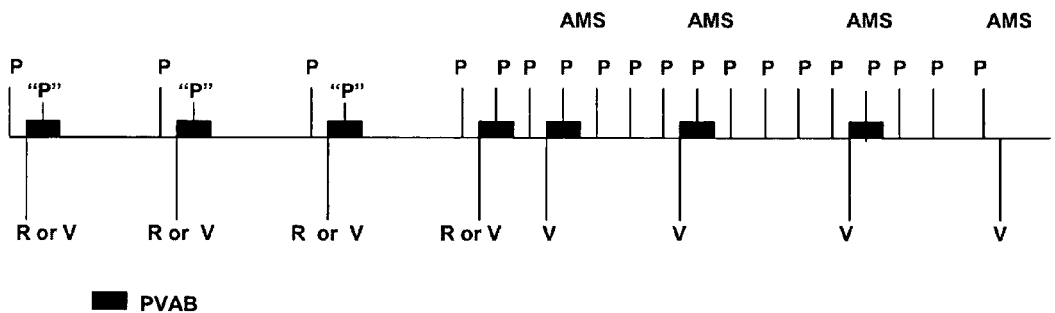
FIG. 4 is a schematic diagram where "P" (on the left side of the figure) represents the far field signal (FFRW) which is prevented from being detected by the PVAB. The system responds to a true tachycardia with appropriate AMS.

FIG. 4 is a schematic diagram where "P" (on the left side of the figure) represents the far field signal (FFRW) which is prevented from being detected by the PVAB of sufficient duration. A portion of the diagram (i.e. the right portion having the multiple, closely-spaced P components) represents the patient's own fast heart rhythm, which is recognized by the system. Responsively, the system appropriately switches into AMS (i.e. non-tracking mode).

Figure 5:
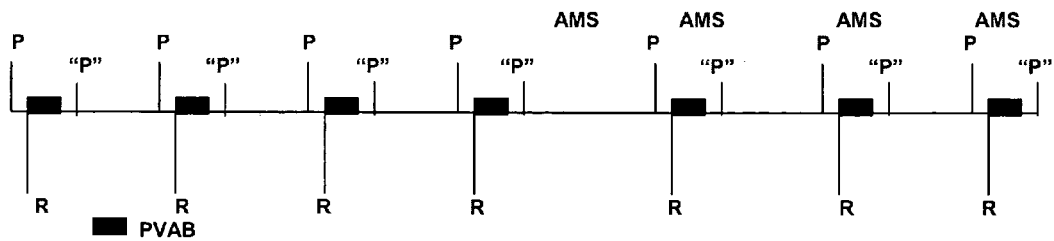
FIG. 5 is a schematic diagram that illustrates what can happen if the PVAB is too short with inappropriate AMS in response to FFRW sensing.

FIG. 5 is a schematic diagram that illustrates what can happen if the PVAB is too short. Here, the far field signal (FFRW) is consistently sensed. After a short period of time, the pacemaker reads the atrial rate as being very fast (i.e. the interval between P to "P", and "P" to P) which causes the system to switch to a non-tracking mode.

Figure 6:
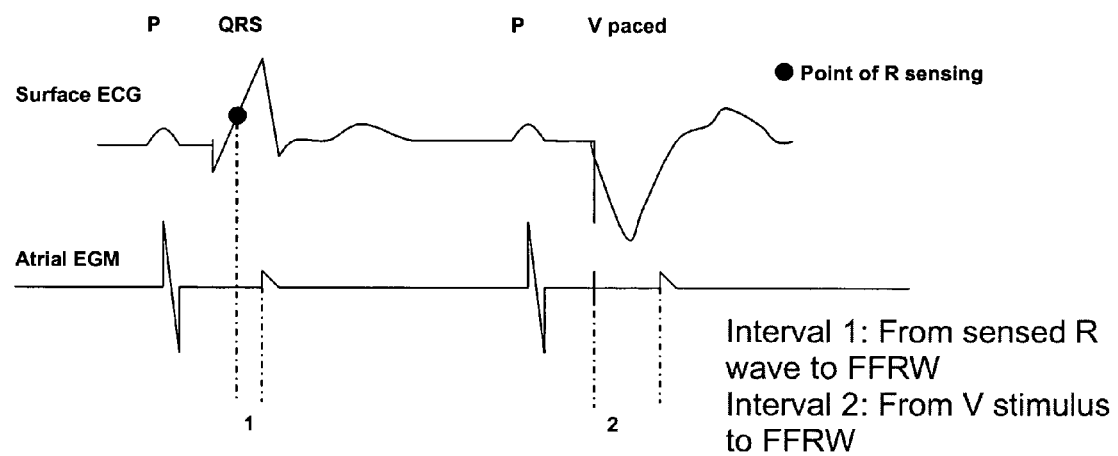
FIG. 6 is a schematic diagram that shows that the interval from the point of sensing of the QRS complex to the FFRW (interval 1) is usually significantly shorter than the interval from the ventricular pacing stimulus in the setting of the V-paced beat to the FFRW (interval 2).

FIG. 6 is a schematic diagram that shows that the interval from the point of sensing of the QRS complex to the FFRW (interval 1) is usually significantly shorter than the interval from the ventricular pacing stimulus in the setting of the V-paced beat to the FFRW (interval 2).

Figure 7:
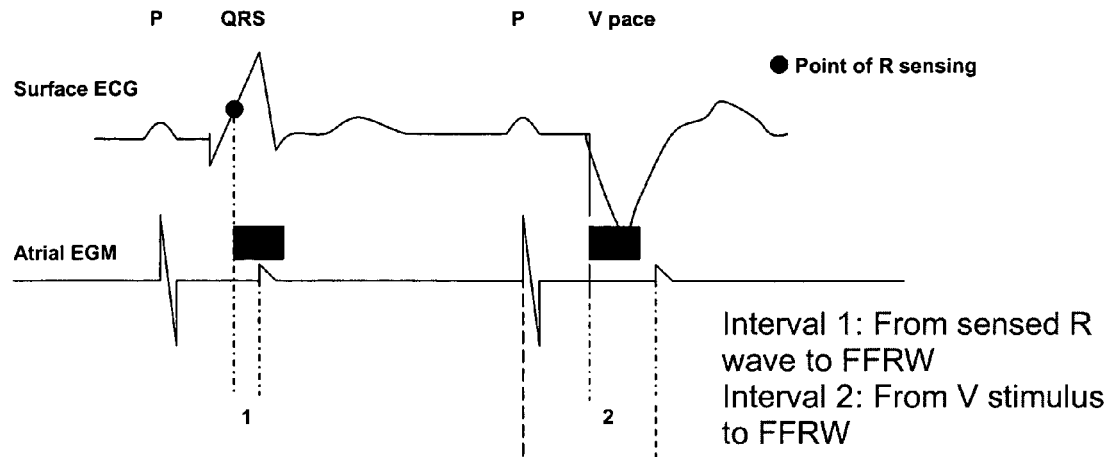
FIG. 7 is a schematic diagram that illustrates a pacemaker programmed with a short PVAB which will prevent sensing of the FFRW associated with the native QRS complex (left side of the figure).

FIG. 7 is a schematic diagram that illustrates a pacemaker programmed with a short PVAB which will prevent sensing of the FFRW associated with the native QRS complex (left side of the figure). However, if the patient starts receiving V-pacing, the FFRW will fall outside of the PVAB and will be sensed and potentially trigger inappropriate mode switching. In the setting of intact AV nodal conduction, the pacemaker reverting to a non-tracking mode will not cause the patient any adverse symptoms. In the patient with even intermittent AV block, reversion to a non-tracking mode will result in loss of appropriate AV synchronization and both symptoms and hemodynamic compromise.

Figure 8:
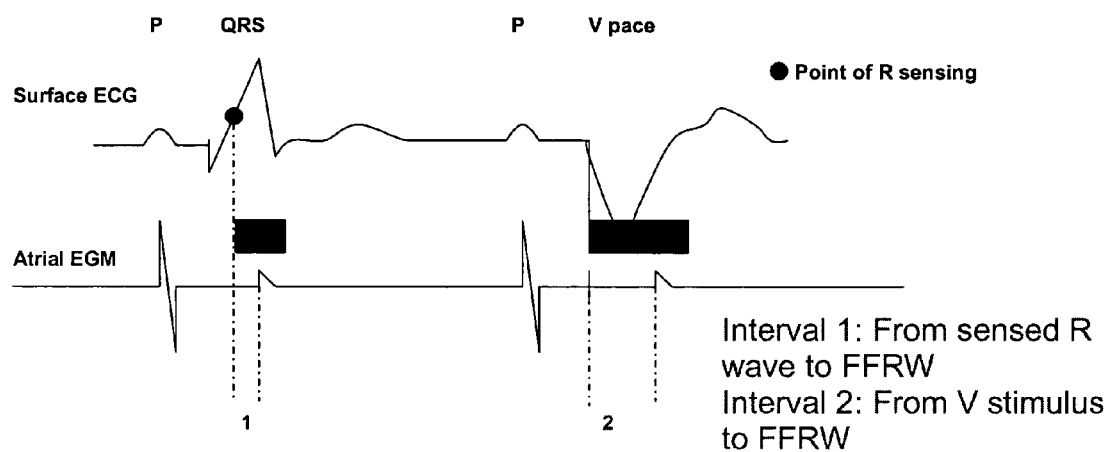
FIG. 8 is a schematic diagram that illustrates a surface ECG and atrial ECM of a device programmed in accordance with one embodiment.

FIG. 8 is a schematic diagram that illustrates a surface ECG and atrial EGM of a device programmed in accordance with one embodiment. Here, the device is programmed in the setting of standard DDD(R) pacing to allow for independent programmability of the PVAB following either a sensed event (R sense) or paced event (V pace). In the setting of intact AV nodal conduction, the shorter PVAB will maximize the system's ability to detect atrial tachyarrhythmias, yet not predispose to identification of a pseudo-atrial tachyarrhythmia in the setting of PV or AV paced rhythm.

Figure 9:
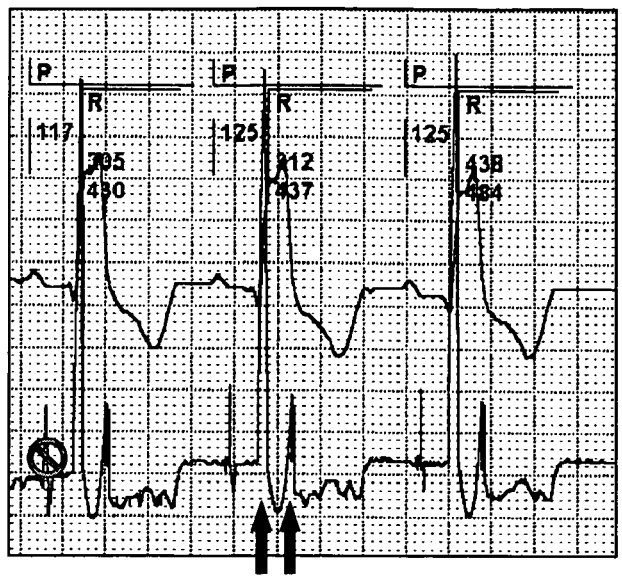
FIG. 9 is a schematic diagram that illustrates a dual site ventricular pacing system with a demonstration of two distinct depolarization signals on a telemetered electrogram associated with a single ventricular depolarization in a patient implanted with a biventricular pacing system.

FIG. 9 is an actual telemetered Ventricular EGM from a dual site ventricular pacing system with a demonstration of two distinct depolarization signals on a telemetered electrogram from a patient implanted with a biventricular pacing system. The middle channel in the diagram is the surface ECG, and the bottom channel is the ventricular electrogram. This patient had P waves detected on the ventricular lead. Note the two distinct electrical depolarizations coinciding with the native QRS although only one (R) is identified by the markers. The second coincided with the absolute refractory period of the ventricular channel but if the conduction delay between the two ventricles was greater or the absolute refractory period, in this case, were shorter—there would be two distinct sensed events for the same QRS complex. In an ICD, this would, after a sufficient number of cycles, fulfill the criteria for either VT or VF resulting in the delivery of therapy that should not have been warranted based on the true rhythm. Although the FIG. 9 electrogram is recorded from a biventricular system, the same phenomena can occur with a dual lead atrial pacing system resulting in a normal rhythm being labeled a tachycardia.

Figure 10:
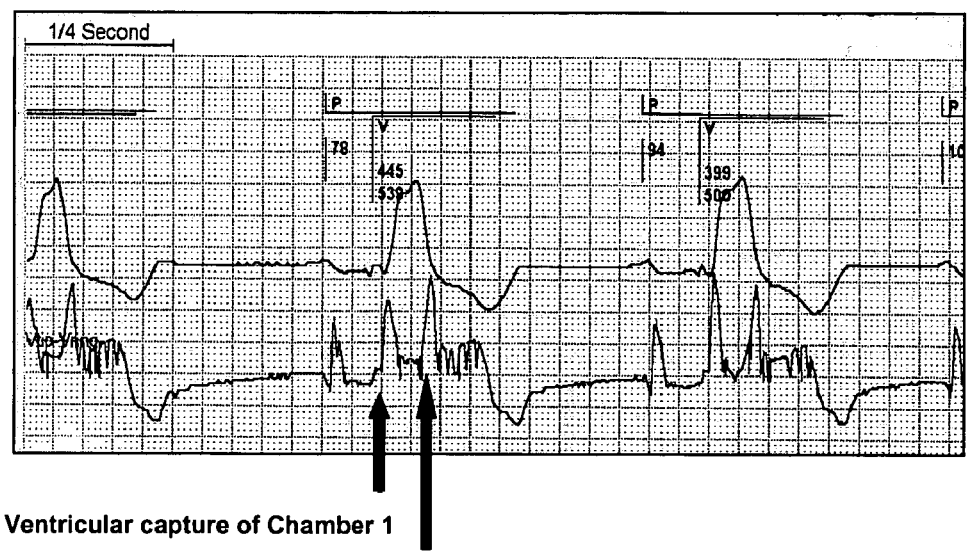
FIG. 10 is a schematic diagram that illustrates a dual site ventricular pacing system where pacing stimuli are delivered to both chambers but only captures one chamber, and there is a delay in conduction to the other chamber allowing a second signal to be sensed at a very short coupling interval to the paced ventricular complex.

FIG. 10 is another actual telemetered ventricular EGM from a dual site biventricular pacing system where pacing stimuli are delivered to both chambers but there is loss of capture in one of the chambers, and there is a delay in conduction to the other chamber that was not captured by the output pulse. If the ventricular refractory period is programmed to a very short interval, this second depolarization occurring at a very short interval between the ventricular stimulus and the "sensed R wave" will be equivalent to a very rapid ventricular rate. This may be labeled as either VT or VF resulting in the inappropriate delivery of therapy. Although the FIG. 10 electrogram is recorded from a biventricular system, the same phenomena can occur with a dual lead atrial pacing system resulting in an atrial paced rhythm where there is loss of capture in one atrial chamber with a tachycardia diagnosed based on the short coupling interval between the atrial output pulse and the subsequent detected (sensed) atrial event.

Table 1, just below, summarizes how, in accordance with one embodiment, the absolute refractory period for a second chamber can be independently programmable in accordance with whether a first chamber is paced or sensed. That is, as the conduction delay may vary depending on which chamber is paced or sensed first, the absolute refractory (blanking)

period for the second chamber is made to be programmable. In accordance with this embodiment, the refractory period of the second chamber starts with the event on the first chamber.

TABLE 1

| Chamber Paced/Sensed | Second Chamber Sensed | Absolute Refractory Period |
|---|---|---|
| Atrial Lead 1 Paced | Atrial Lead 2 Sensed | Period A on Lead 2 started by Lead 1 paced event |
| Atrial Lead 1 Paced | Atrial Lead 2 Sensed | Period B on Lead 2 started by Lead 1 sensed event |
| Atrial Lead 2 Paced | Atrial Lead 1 Sensed | Period C on Lead 1 started by Lead 2 paced event |
| Atrial Lead 2 Paced | Atrial Lead 1 Sensed | Period D on Lead 1 started by Lead 2 sensed event |
| RV Paced | LV Sensed | Period E on LV lead started by RV paced event |
| RV Sensed | LV Sensed | Period F on LV lead started by RV sensed event |
| LV Paced | RV Sensed | Period G on RV lead started by LV paced event |
| LV Sensed | RV sensed | Period H on RV lead started by LV sensed event. |

Periods A, B, C, and D can be either different in each case or the same. These absolute refractory (blanking) periods may also be automatically adjusted based on sensor-input to the pacemaker, rate or other factors having started from their programmed baseline values. In addition to the absolute refractory (blanking) period, there will be a standard relative refractory period, also called a noise sampling period, added to the blanking period. The microprocessor will allow for detection of signals during the relative refractory period for either noise-mode function or tachyarrhythmia detection. The reason for labeling the Atrial Leads as "1" and "2", rather than RA and LA, is that an increasing number of physicians are utilizing dual-site atrial pacing which usually involves one lead positioned in the high right atrium and the second lead placed at the ostium of the coronary sinus. Hence, both leads are in the right atrium.

AMS Algorithm in Standard DDD(R) Pacemaker—Far Field R Wave Detection

Figure 11:
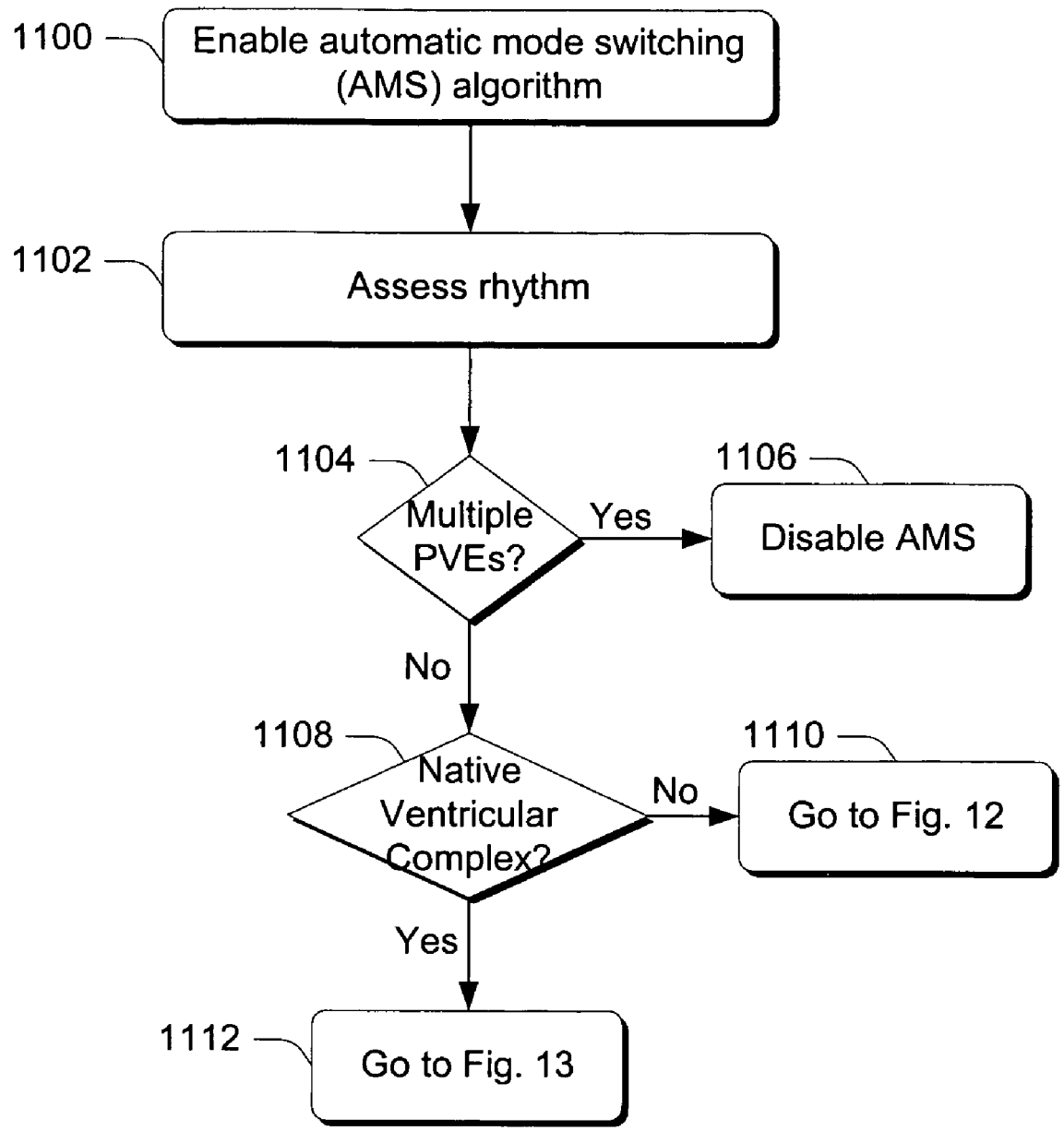
FIGS. 11-13 are flow diagrams that describe steps in a method in accordance with one embodiment.
Figure 12:
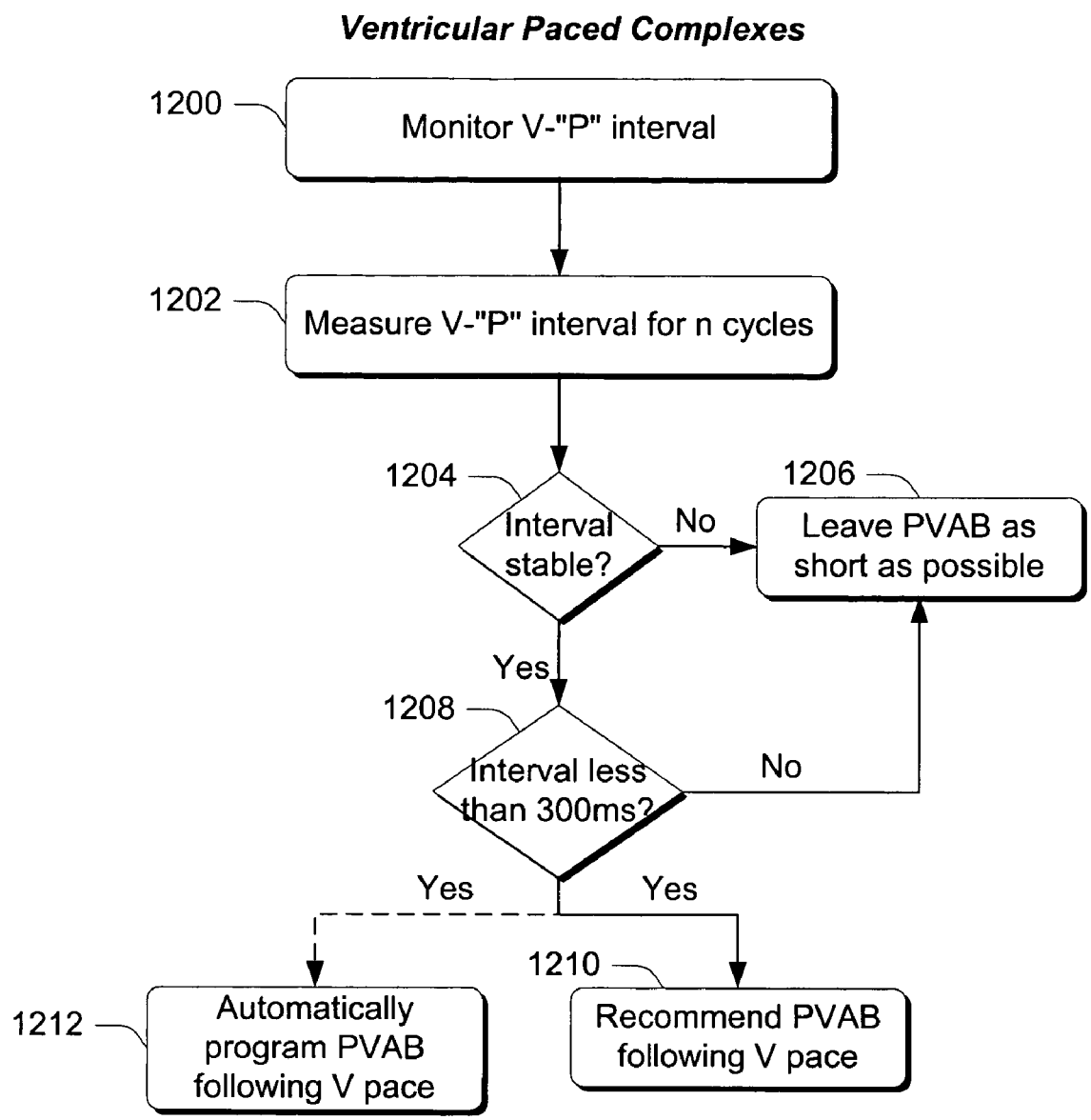
Figure 13:
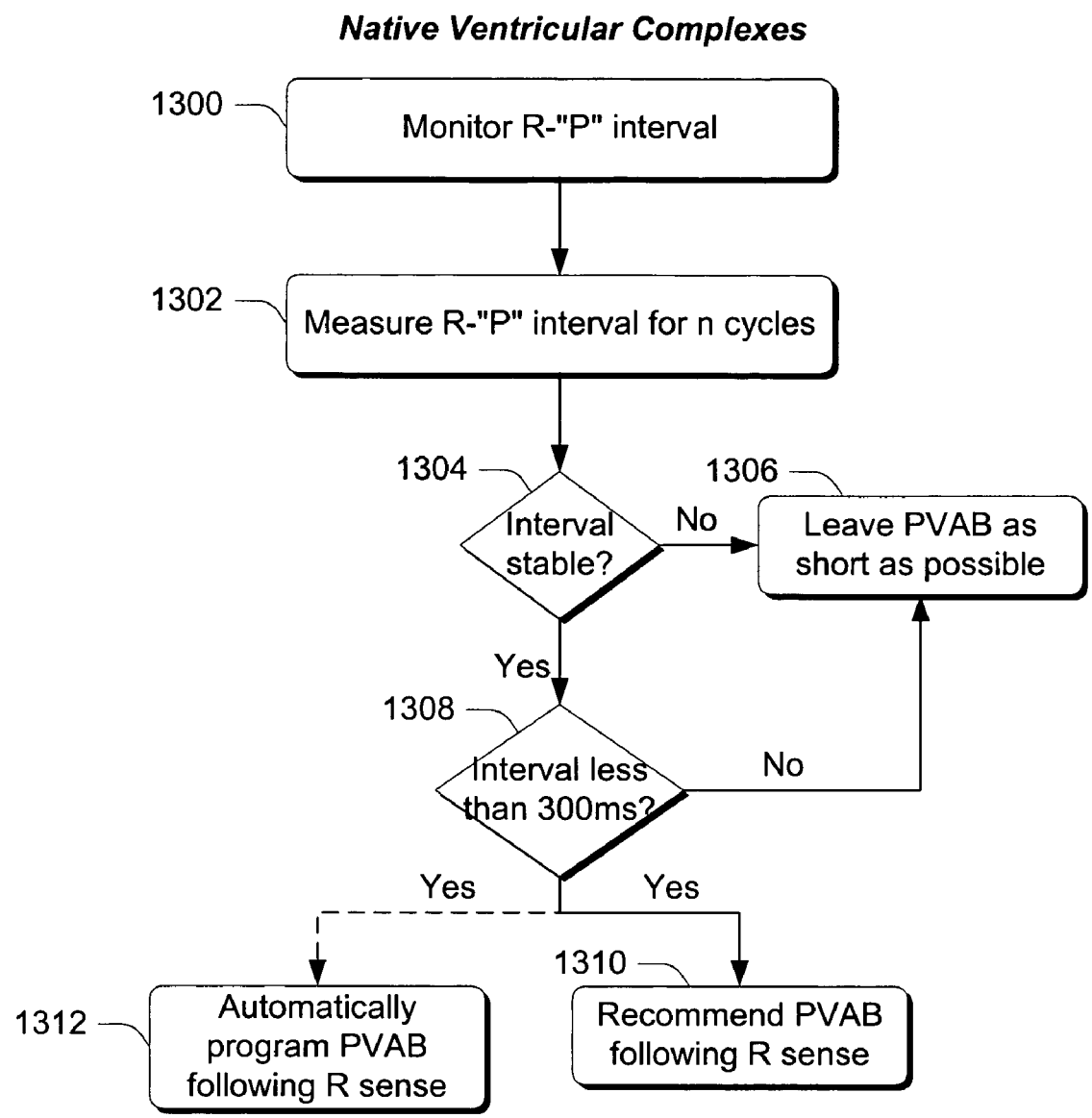

FIGS. 11-13 are flow diagrams that describe steps in a method in accordance with one embodiment. The method provides an automatic mode switching algorithm in DDD pacing with far field R wave detection. DDD pacing refers to a dual-chamber pacing with atrial tracking—which is pacing and sensing in both atrium and ventricle with dual response (inhibited or triggered) to sensing. In the absence of intrinsic activity, both chambers are paced at the programmed base rate. Intrinsic atrial activity during the atrial alert period inhibits the atrial output, terminates the atrial escape interval and initiates the AV delay. DDD(R) pacing refers to dual-chamber pacing with atrial tracking and rate modulation.

Step 1100 enables an automatic mode switching algorithm and step 1102 assesses the patient's rhythm. Step 1104 determines whether there are multiple premature ventricular events (PVEs) also clinically known as premature ventricular complexes (PVCs). If there are, then step 1106 disables the AMS algorithm. If, on the other hand, step 1104 determines that there are not multiple PVEs, step 1108 determines whether the patient is experiencing native ventricular complexes. Within DDD pacing, there are four primary states or event combinations which are: PV (sensed P-wave followed by a ventricular output pulse), PR (sensed P-wave followed by a sensed R-wave), AV (atrial pulse followed by a ventricular output pulse), and AR (atrial output pulse followed by a sensed R-wave). Native ventricular complexes correspond to the PR and AR states, while non-native ventricular complexes correspond to the PV and AV states.

If the patient is not experiencing native ventricular complexes (e.g. the patient is experiencing PV or AV), then step 1110 branches to FIG. 12 for a first set of actions to program the PVAB parameter. If, on the other hand, the patient is experiencing native ventricular complexes (e.g. the patient is experiencing PR or AR), step 1112 branches to FIG. 13 for a second set of actions to program the PVAB parameter.

Referring to FIG. 12 and responsive to the patient experiencing a ventricular paced complex (i.e. PV or AV), step 1200 monitors the patient's V-"P" interval and step 1202 measures the V-"P" interval for n cycles. Here, "P" is used to indicate a P-wave that may be occurring in the refractory period. Step 1204 determines whether the measured interval is stable. The term "stable" can mean either that every measured interval is stable, or some x out of y number of intervals are stable. By stable, it is meant that measured interval as described above is either an exact interval or + or − a number of milliseconds with respect to a preset or programmable mean interval (e.g. 20 ms). If the interval is not stable, then step 1206 leaves the PVAB as short as possible. If, on the other hand, the interval is stable, step 1208 determines whether the interval is less than a pre-determined value. Here, the pre-determined value is equal to 300 ms. If the interval is not less than the pre-determined value, the method leaves the PVAB as short as possible. If, on the other hand, the interval is less than the pre-determined value, one of two things can occur. Step 1210 can recommend a PVAB value following the V pace event. Such might be done in the context of the next follow-up evaluation. Alternately or additionally, step 1212 can automatically program the PVAB following the V pace event.

Referring to FIG. 13 and responsive to the patient experiencing a native ventricular complex (i.e. PR or AR), step 1300 monitors the patient's R-"P" interval and step 1302 measures the R-"P" interval for n cycles. Step 1304 determines whether the measured interval is stable. If not, step 1306 leaves the PVAB as short as possible. If, on the other hand, step 1304 determines that the measured interval is stable, then step 1308, step 1308 determines whether the interval is less than a pre-determined value. Here, the value is selected to be 300 ms. If the interval is not less than the pre-determined value, then step 1306 leaves the PVAB as short as possible. If, on the other hand, the interval is less than the pre-determined value, one of two things can occur. Step 1310 can recommend a PVAB value following the R sense event. Such might be done in the context of the next follow-up evaluation. Alternately or additionally, step 1312 can automatically program the PVAB following the R sense event. For example, if the R-"P" interval is 225 ms, then a PVAB of 250 ms might either be recommended or automatically programmed.

As a further consideration, consider the following. Depending on the pacing state, the device is not going to pick up native and paced ventricular complexes at the same time. In each case, however, the device will want to complete its far field R wave detection.

As an example, consider that if the AV delay is sufficiently long that the ventricular channel is inhibited so that the device always detects an R wave, what the device will want to do is to complete its R-"P" FFRW detection. To do this, the AV or PV interval is shortened to around 50 ms so that the device can be forced to ventricularly pace the patient. Once the patient is being ventricularly paced, the device can initiate the method set forth in FIG. 12, so that it can assess what the FFRW detection would be with ventricular pacing.

By the same token, if the device is always V-pacing such that the method of FIG. 12 is executed, then the device will want to complete its R-"P" FFRW detection associated with a ventricular sensed event. To do this, the device can temporarily extend the AV or PV delay to the maximum allowed which, in turn, allows assessment of the rhythm for R-sensing. If there is no R sensing, then the device can terminate its effort to measure the R-"P" interval. If, on the other hand, there is an R sense (i.e. a native ventricular complex) with the increase in AV delay, the method branch to FIG. 13 so that it can assess what the FFRW detection would be in the context of native ventricular complexes.

Multisite Atrial Stimulation—AMS—Parallel Circuit

Figure 14:
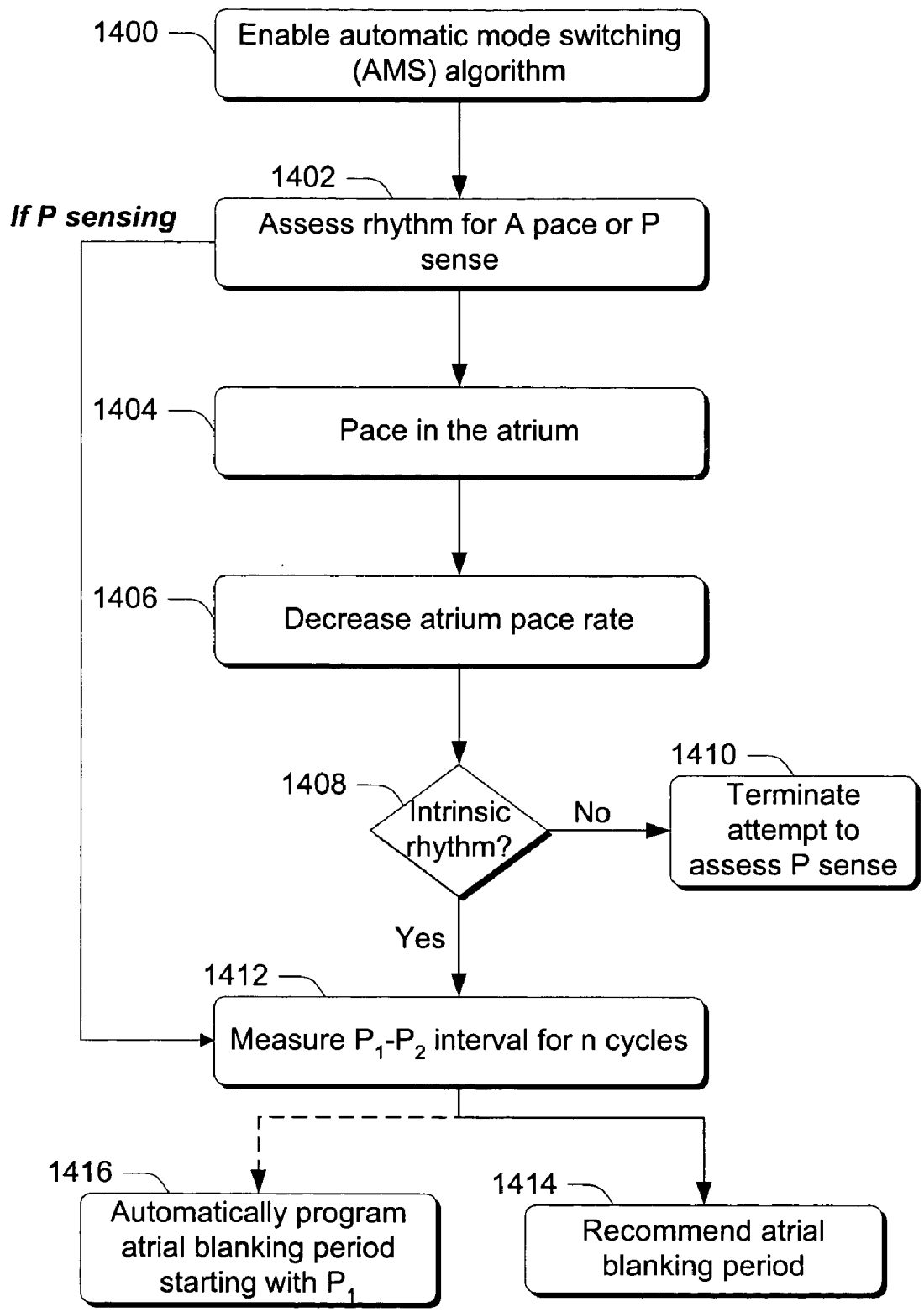
FIG. 14 is a flow diagram that describes steps in a method that is employed in connection with multisite atrial stimulation that utilizes a parallel circuit.

FIG. 14 is a flow diagram that describes steps in a method that is employed in connection with multisite atrial stimulation that utilizes a parallel circuit. That is, currently most if not all stimulation devices employ a bifurcated adapter in order to get two leads (such as two atrial leads) connected into the device. Essentially the bifurcated adapter enables the leads to utilize the same actual channel in the device. Typically then, there is only one atrial output sensing circuit and one ventricular output sensing circuit. So, when the device paces in the atrium, the signal travels down both atrial leads simultaneously. When the atrial leads sense, the channel typically picks up one complex from a first of the leads, and then later the same complex from the other of the leads. The P-wave sensed by the first atrial lead is referred to as P1, and the P-wave sensed by the second atrial lead is referred to as P2. However, the parallel output system cannot determine which lead (right or left) is the source of the first or second signal as there is a common sensing circuit shared by both leads.

Step 1400 enables the automatic mode switching (AMS) algorithm, and step 1402 assess rhythm for atrial pacing or P sensing. That is, with respect to multisite atrial stimulation, the patient can either be paced in the atrium, or they can have intrinsic activity which generates an intrinsic P-wave. If the patient has intrinsic activity in the atrium such that they are not being paced, then step 1402 branches to step 1412 which measures the P1-P2 interval for n cycles. After measuring the interval for n cycles, a couple of different things can happen. First, step 1414 can recommend an atrial blanking period. Alternately or additionally, step 1416 can automatically program an atrial blanking period starting with P1.

If, on the other hand, there is pacing in the atrium (as in step 1404), step 1406 decreases the atrium pace rate in an attempt to determine whether the patient has an intrinsic activity. By decreasing the atrial pacing rate, an attempt is made to unmask the patient's own intrinsic rhythm so that the device can measure the P-waves. Step 1408 determines whether, in light of decreasing the atrial pacing rate, whether there is any intrinsic rhythm. This step is carried out with no blanking period. If there is not, step 1410 terminates the attempt to assess the P-sense (or the attempt to assess the patient's intrinsic P-waves). In an attempt to ascertain whether there is any intrinsic rhythm, steps 1406 and 1408 can loop back and forth in the event no intrinsic rhythm is found. Doing so can decrease the atrial pacing rate to the lowest rate allowed. If step 1408 determines that there is intrinsic rhythm, step 1412 measures the P1-P2 interval for n cycles. After measuring the interval for n cycles, a couple of different things can happen. First, step 1414 can recommend an atrial blanking period. Alternately or additionally, step 1416 can automatically program an atrial blanking period starting with P1.

Multisite Atrial Stimulation—AMS—Independent Circuit

Current movement in the pacing industry is towards completely independent leads in the atrium that are programmable and controllable with dedicated, independent circuits. Having independent leads in the atrium raises some additional considerations when setting the blanking period.

Step 1500 enables an automatic mode switching (AMS) algorithm and step 1502 assess rhythm for either atrial pacing on channel 1 or P sensing on channel 1. If the device is A pacing on channel 1, then the device will want to compute a blanking period for channel 2. Accordingly, step 1504 measures the A1-P2 interval (i.e. the interval between the atrial output pulse on channel 1 and the signal that is detected on channel 2). Now, a couple of different things can occur. First, step 1506 can recommend an atrial blanking period on P2 starting with A1. Alternately or additionally, step 1508 can automatically program an atrial blanking period for P2 starting with A1.

Assume now that at step 1502, the device is P sensing on channel 1. That is, the device is sensing native P wave events on channel 1. If this is the case, step 1512 measures the P1-P2 interval for n cycles. Now, step 1514 can recommend an atrial blanking period on P2 starting on P1. Alternately or additionally, the device can automatically program an atrial blanking period for P2 starting with P1.

Now, assume that the patient is being atrially paced on channel 1, after the device measures A1-P2, step 1510 can decrease the pacing rate on channel 1 to attempt to ascertain whether there are any native events that are coming from the atrium and being detected on channel 1. Accordingly, step 1510 decreases the rate and returns to step 1512 to attempt to ascertain a blanking period on P2.

Additionally, the device can further attempt to define atrial blanking periods for other permutations of multisite atrial pacing. As an example, consider the following.

If the patient is being atrially paced on channel 1, and the device wants to determine the atrial blanking period on channel 1, the device can increase the pacing rate and start atrially pacing on channel 2. The device can then measure the A2-P1 interval (the interval between the atrial pacing output on channel 2 and the signal on channel 1) and either recommend or program an atrial blanking period on P1 beginning with A2.

Figure 15:
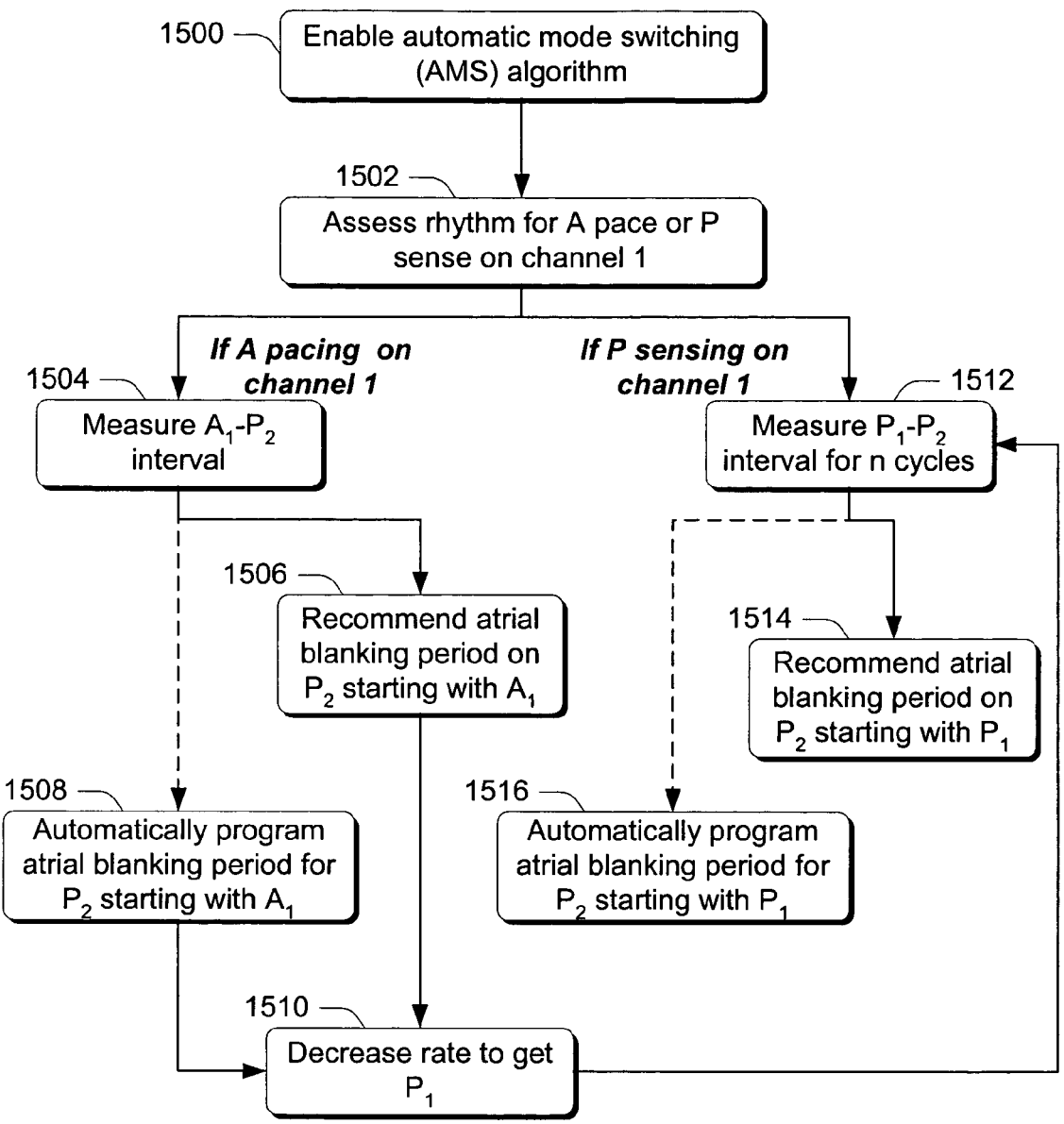
FIG. 15 is a flow diagram that describes steps in a method that is employed in connection with multisite atrial stimulation that utilizes an independent circuit.

Further, if the device is P sensing on channel 1, the pacing rate can be increased on channel 1 to effect atrial pacing on channel 1 and measurements can proceed as described in FIG. 15. Then, the atrial rate can be increased on channel 2 for atrial pacing on channel 2. Measurements can then proceed as described above in FIG. 15. In this case, measurement of the A2-P1 interval would take place (i.e. the interval between the atrial pacing output on channel 2 and the signal on channel 1).

If the device is P sensing on channel 1 or 2, the device will still be able to assess the other channel because the two channels are independent. This can be achieved if the blanking period is temporarily reduced to 0 (zero) as this will be dependent on the native activation sequence, and the pacing system will not be able to alter this. The system will be able to determine which lead detects the signal first (P1 or P2) and then, set the blanking period of the other complex beginning with the first complex. Given that the signals are native, one will not be able to assess the alternate relationship as if the complex that was sensed second is then sensed first. However, in this setting, the device can recommend or automatically program the same blanking period as based on the P sensed subroutine of FIG. 15.

The methodology described above can be utilized in the context of a system that includes more than two electrodes (i.e. 2+x) in a given chamber. For example, it is conceivable that in the future, there may be three, four, five or even more electrodes in a given chamber. Thus, the above analysis can be expanded to include all of these possibilities. For example, if the signal is sensed on P1 first, then we can measure the time to P2 to set the blanking period for P2, the time to P3 in order to set the blanking period for P3, the time to Pn to set the blanking period for Pn.

Multisite Ventricular Pacing—Prevention of Double Counting to Prevent Misdiagnosis of Ventricular Tachycardia—Independent Channels In much the same way that atrial blanking periods can be defined for the atrial channels, ventricular blanking periods can be defined for the ventricular channels in connection with multisite ventricular pacing. As an example, consider FIG. 16.

Step 1600 enables a ventricular tachycardia (VT) detection algorithm. Step 1602 assess rhythm for either ventricular pacing or R sensing (i.e. intrinsic activity) on channel 1. If the device is ventricularly pacing on channel 1, step 1604 measures the V1-R2 interval. Based on the measured interval, the device can recommend, at step 1606, a ventricular blanking period on R2 starting with V1. Alternately or additionally, step 1608 can automatically program the ventricular blanking period for R2 starting with V1. If, on the other hand, the device is R sensing on channel 1 (that is, sensing intrinsic activity on channel 1), then step 1612 measures the R1-R2 interval for n cycles while the blanking period is temporarily disabled or reduced to 0 (zero). During this period of measurement, the potential rates are not used to diagnose a tachyarrhythmia or deliver therapy. Based on this interval, step 1614 can recommend a ventricular blanking period on R2 starting with R1. Alternately or additionally, step 1616 can automatically program the ventricular blanking period for R2 starting with R1.

If the device is ventricularly pacing on channel 1, the device will want to establish a ventricular blanking period on channel 1. To do this, the device can increase the pacing rate and start ventricularly pacing on channel 2. The device can then measure the V2-R1 interval, and either recommend or program the blanking period on R1 beginning with V2.

If the device is ventricularly sensing on channel 1, the device can increase the pacing rate on channel 1 to effect V pacing on channel 1. The device can then increase the ventricular rate on channel 2 for V pacing on channel 2 and proceed with measurements as set forth in FIG. 16.

If the device is R sensing on channel 1 or 2, the device will not be able to assess the other channel, as this will be dependent on the native activation sequence and the pacing system will not be able to alter this. However, in this setting, the device can recommend or autoprogram the same blanking period as based on the R sensed subroutine above.

The methodology described above can be utilized in the context of a system that includes more than two electrodes (i.e. 2+x, where x>0) in a given chamber. For example, it is conceivable that in the future, there may be three, four, five or even more electrodes in a given chamber. Thus, the above analysis can be expanded to include all of these possibilities. For example, if the signal is sensed on R1 first, then we measure the time to R2 to set the blanking period for R2, the time to R3 in order to set the blanking period for R3, the time from R1 to Rn to used to set the blanking period for Rn.

Figure 17:
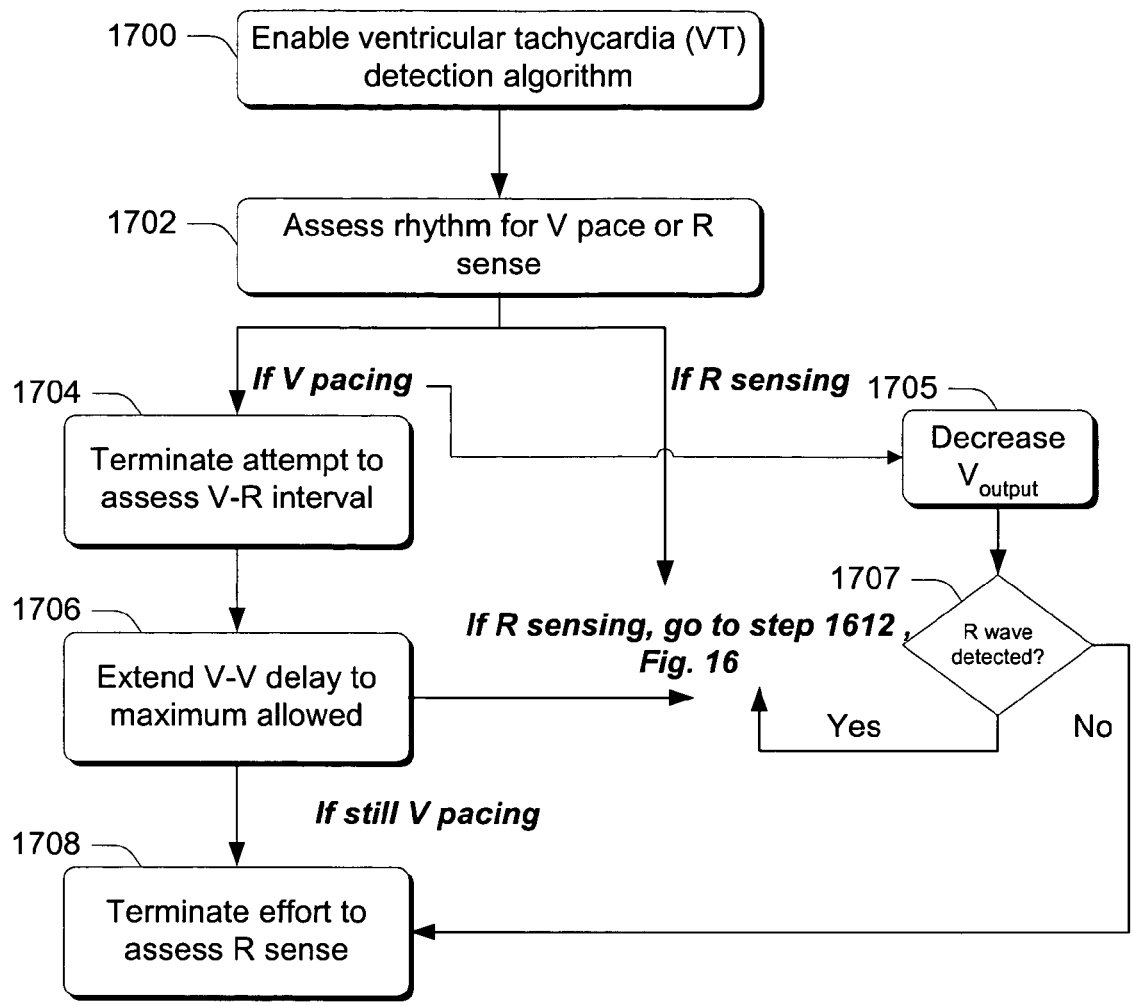
FIG. 17 is a flow diagram that describes steps in a method that is employed in connection with multisite ventricular pacing that utilizes parallel channels.

Multisite Ventricular Pacing—Prevention of Double Counting to Prevent Misdiagnosis of Ventricular Tachycardia—Parallel Channels FIG. 17 is a flow diagram that describes processing in connection with multisite ventricular pacing utilizing a device that has parallel ventricular channels—that is, ventricular channels that are not independently controllable.

Step 1700 enables a ventricular tachycardia (VT) detection algorithm. Step 1702 assesses the patient's rhythm for either V pacing or R sensing. In the event that the patient is being ventricularly paced, step 1704 terminates an attempt to assess the patient's V-R interval. This is because the pacing output goes to both channels simultaneously. Step 1706 extends the AV delay to the maximum. If the device is R sensing on channel 1, then the method branches to step 1612 in FIG. 16 for purposes of establishing or recommending a ventricular blanking period. If, however, the device still ventricularly paces with the AV delay at the maximum allowable, then step 1708 terminates the effort to assess the R sense.

Figure 16:
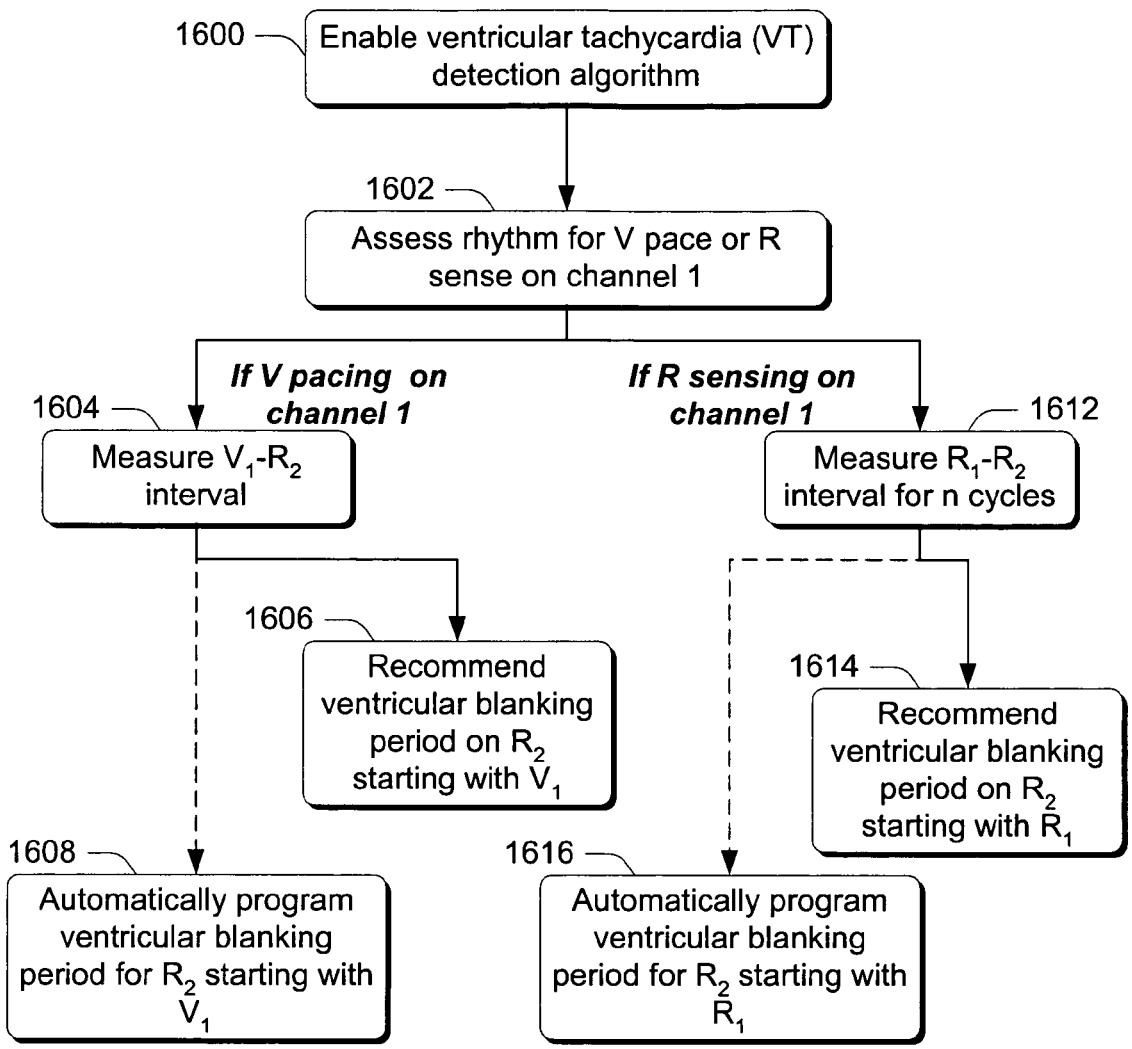
FIG. 16 is a flow diagram that describes steps in a method that is employed in connection with multisite ventricular pacing that utilizes independent channels.

If, at step 1702, the device is R sensing—that is, sensing intrinsic activity in the ventricles, then the method branches to step 1612 in FIG. 16 for purposes of establishing or recommending a ventricular blanking period.

With R sensing, the device is sensing intrinsic activity. Which ever channel experiences the initial sensing is not a controllable parameter. Thus, the device can only measure the interval between the complex on channel 1 and the complex on channel 2.

In a parallel system during V pacing, there may be loss of capture on one of the chambers. As such, even though the stimulus is delivered to that chamber, (e.g. V2), it does not capture. This allows the capture beat on V1 to be conducted to the other chamber resulting in an R2 that, if it falls outside the blanking period, will be sensed and potentially result in a diagnosis of a tachyarrhythmia. To address this possibility, if, at step 1702, the device is delivering a ventricular output, the method branches to step 1705 where the output is reduced until a V-R complex is detected and the blanking period is temporarily canceled or reduced to zero (0). If an R wave is detected, then the method returns to step 1612 (FIG. 16). If, at step 1707, no R wave is detected, the method proceeds to step 1708 and terminates the effort to assess R sense. As one chamber is likely to have a lower output than the other chamber, one cannot repeat this process on the chamber that has the higher output as that will also capture the chamber with the lower output.

CONCLUSION

Various embodiments described above can reduce inappropriate tachyarrhythmia detection and hence an inappropriate response to a normal rhythm. In the case of the atrial channel, mode switching in response to inappropriate but anticipated signals, such as far field R-waves can be prevented. Various embodiments can also increase the alert period for detection of true atrial tachyarrhythmias in dual chamber pacing systems. Various embodiments can reduce mode switching or tachyarrhythmia response to same chamber delayed signals. Various embodiments can increase the alert period for detection of true tachyarrhythmias in multisite pacing systems, be it atrial multisite pacing or ventricular multisite pacing while at the same time, minimizing inappropriate detection of the same native event at multiple different sites and falsely labeling the closely spaced signals as a pathologic tachycardia.

Although the invention has been described in language specific to structural features and/or methodological steps, it is to be understood that the invention defined in the appended claims is not necessarily limited to the specific features or steps described. Rather, the specific features and steps are disclosed as preferred forms of implementing the claimed invention.

What is claimed is:

1. A method comprising:
   configuring an implantable stimulation device to effect multisite ventricular pacing using first and second channels;

configuring the stimulation device to have a first variable blanking period on the first channel that is greater than zero if an event detected on the second channel is a sensed event;

configuring the stimulation device to begin the first blanking period in direct response to the detection of the sensed event and prior to delivery of an intervening pacing pulse; and configuring the stimulation device to have a second variable blanking period on the first channel if an event detected on the second channel is a paced event.

2. The method of claim 1 further comprising configuring the stimulation device to have a variable blanking period on the second channel depending on whether an event detected on the first channel is paced or sensed.

3. The method of claim 1 further comprising configuring the stimulation device with a ventricular tachycardia detection algorithm.

4. The method of claim 1, wherein configuring the device to have a variable blanking period comprises configuring the device to be manually programmable.

5. The method of claim 1, wherein configuring the device to have a variable blanking period comprises configuring the device to automatically select the blanking period.

6. The method of claim 1, wherein configuring the device to have a variable blanking period comprises configuring the device to make a recommendation as to the variable blanking period.

7. The method of claim 1 further comprising:
configuring the stimulation device to have a variable blanking period on the second channel depending on whether an event on the first channel is paced or sensed; and
wherein configuring the device to have a variable blanking period comprises configuring the device to be manually programmable.

8. The method of claim 1 further comprising:
configuring the stimulation device to have a variable blanking period on the second channel depending on whether an event on the first channel is paced or sensed; and
wherein configuring the device to have a variable blanking period comprises configuring the device to automatically select the blanking periods.

9. The method of claim 1 further comprising:
configuring the stimulation device to have a variable blanking period on the second channel depending on whether an event on the first channel is paced or sensed; and
wherein configuring the device to have a variable blanking period comprises configuring the device to make a recommendation as to the variable blanking period.

10. A method comprising:
providing an implantable stimulation device to effect multisite ventricular pacing using separate channels, the separate channels comprising at least one separately controllable ventricular lead;
ventricularly pacing a patient using the separate channels;
selecting a first variable blanking period on a ventricular lead on a first channel if an event at a second of the ventricular leads on a second channel is a paced event;
selecting a second variable blanking period that is greater than zero in the ventricular lead on the first channel in response to detection of a sensed event at the second of the ventricular leads on the second channel; and
beginning the first blanking period in direct response to the detection of the sensed event and prior to delivery of an intervening pacing pulse.

11. The method of claim 10 further comprising selecting a blanking period on the second of the ventricular leads on the second channel depending on whether an event at the first of the ventricular leads is paced or sensed.

12. The method of claim 10 further enabling a ventricular tachycardia detection algorithm on the stimulation device.

13. The method of claim 10, wherein selecting the blanking period comprises manually programming the blanking period.

14. The method of claim 10, wherein selecting the blanking period comprises automatically selecting the blanking period.

15. The method of claim 10, wherein selecting the blanking period is performed, at least in part, by the stimulation device making a recommendation as to the variable blanking period.

16. The method of claim 10 further comprising:
selecting a blanking period on the second of the ventricular leads on the second channel depending on whether an event at the first of the ventricular leads is paced or sensed; and
wherein selecting the blanking periods comprise manually programming the blanking periods.

17. The method of claim 10 further comprising:
selecting a blanking period on the second of the ventricular leads on the second channel depending on whether an event at the first of the ventricular leads is paced or sensed; and
wherein selecting the blanking periods is performed by the stimulation device automatically selecting the blanking periods.

18. The method of claim 10 further comprising:
selecting a blanking period on the second of the ventricular leads on the second channel depending on whether an event at the first of the ventricular leads is paced or sensed; and
wherein selecting the blanking periods are performed, at least in part, by the stimulation device making a recommendation as to the variable blanking period.

19. An implantable stimulation device comprising:
a ventricular lead comprising at least one electrode and configured for placement in a patient's body in electrical contact with at least one ventricle;
sensing circuitry operative to sense ventricular signals; and
control circuitry operative to select a first variable value for a ventricular blanking parameter if the sensed ventricular signal is a paced event and to select a second variable value that is greater than zero for the ventricular blanking parameter in response to the sensing circuitry sensing a ventricular signal that is a sensed event, wherein the control circuitry is further configured to begin the second blanking parameter in direct response to the sensed event and prior to delivery of an intervening pacing pulse.

20. The method of claim 1 wherein selecting a first variable blanking period comprises selecting a first variable blanking period as a function of an interval between one or more sensed events detected on the second channel and one more events detected on the first channel, and wherein selecting a second variable blanking period comprises selecting a second variable blanking period as a function of an interval between one or more paced events on the second channel and one more events detected on the first channel.

* * * * *